US006869698B2

(12) United States Patent
Chen et al.

(10) Patent No.: US 6,869,698 B2
(45) Date of Patent: Mar. 22, 2005

(54) ORGANIC LIGHT-EMITTING DEVICE USING PARACYCLOPHANE

(75) Inventors: Jian Ping Chen, San Jose, CA (US); Kazunori Ueno, Ebina (JP); Koichi Suzuki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/309,116

(22) Filed: Dec. 4, 2002

(65) Prior Publication Data

US 2004/0110027 A1 Jun. 10, 2004

(51) Int. Cl.$^7$ .............................................. H05B 33/12
(52) U.S. Cl. .................... 428/690; 428/917; 313/504; 313/506
(58) Field of Search ................ 428/690, 917; 313/503, 504, 506; 558/270; 252/301.16

(56) References Cited

U.S. PATENT DOCUMENTS

| | | | |
|---|---|---|---|
| 3,117,168 A | 1/1964 | Gorham | 260/668 |
| 3,616,314 A | 10/1971 | Settineri | 204/59 |
| 3,754,015 A | 8/1973 | Hedaya | 260/456 |
| 4,000,987 A | 1/1977 | Okagami et al. | 48/214 |
| 4,225,647 A * | 9/1980 | Parent | 428/336 |
| 4,675,462 A | 6/1987 | Ungarelli et al. | 585/429 |
| 5,098,807 A | 3/1992 | Shimada et al. | 430/59 |
| 5,233,090 A * | 8/1993 | Shimada et al. | 564/426 |
| 5,250,378 A | 10/1993 | Wang | 430/83 |
| 5,302,767 A | 4/1994 | Galley et al. | 570/184 |
| 5,366,811 A | 11/1994 | Higashi et al. | 428/457 |
| 5,663,407 A | 9/1997 | Shimada et al. | 558/270 |
| 5,712,361 A * | 1/1998 | Stern et al. | 528/86 |
| 5,728,480 A | 3/1998 | Stern et al. | 428/690 |
| 5,757,128 A | 5/1998 | Topp | 313/509 |
| 5,811,177 A | 9/1998 | Shi et al. | 428/209 |
| 5,858,561 A | 1/1999 | Epstein et al. | 428/690 |
| 6,016,033 A | 1/2000 | Jones et al. | 313/506 |
| 6,265,459 B1 | 7/2001 | Mahoney et al. | 522/17 |
| 6,288,162 B2 | 9/2001 | Leugs et al. | 524/560 |
| 6,291,072 B1 | 9/2001 | Kimoto et al. | 428/422 |
| 6,344,283 B1 | 2/2002 | Inoue et al. | 428/690 |
| 6,372,154 B1 | 4/2002 | Li et al. | 252/301.16 |
| 6,380,415 B2 | 4/2002 | Uneyama et al. | 556/478 |
| 6,385,162 B1 | 5/2002 | Nagase et al. | 369/288 |
| 6,392,097 B1 | 5/2002 | Dolbier, Jr. et al. | 564/411 |
| 6,455,693 B1 * | 9/2002 | Lee et al. | 540/145 |

FOREIGN PATENT DOCUMENTS

| | | | |
|---|---|---|---|
| JP | 62-119545 | * | 5/1987 |
| JP | 06-145657 | * | 5/1994 |

OTHER PUBLICATIONS

Reich, H. J., Cram, D. J., "Macro Rings. XXXVII. Multiple Electrophilic Substitution Reactions of [2.2]Paracyclophanes and Interconversions of Polysubstituted Derivatives", J. Am. Chem. Soc., vol. 91, No. 13, pp. 3527–3533 (1969).

Izuoka, A., Murata, S., Sugawara, T., Iwamura, H., "Molecular Design and Model Experiments of Ferromagnetic Intermolecular Interaction in the Assembly of High–Spin Organic Molecules. Generation and Characterization of the Spin States of Isomeric Bis(phenylmethylenyl)[2.2]paracyclophanes," J. Am. Chem. Soc., vol. 109, No. 9, pp. 2631–2639 (1987).

(List continued on next page.)

Primary Examiner—Rena Dye
Assistant Examiner—Camie S Thompson
(74) Attorney, Agent, or Firm—Fitzpatrick, Cella, Harper & Scinto

(57) ABSTRACT

An organic light-emitting device (OLED) in which a paracyclophane or a paracyclophane derivative is used as the emissive layer and/or one or more of the charge transport layers, or as a host material for one or more of these layers.

8 Claims, 1 Drawing Sheet

OTHER PUBLICATIONS

Miyaura, N., Suzuki, A., "Palladium–Catalyzed Cross–Coupling Reactions of Organoboron Compounds", Chem. Rev., vol. 95, No. 7, pp. 2457–2483 (1995).

Bazan, G.C., Oldham, W.J., Jr., Lachicotte, R.J., Tretiak, S., Chernyak, V., Mukamel, S., "Stilbenoid Dimers: Dissection of a Paracyclophane Chromophore", J. Am. Chem. Soc., vol. 120, No. 36, pp. 9188–9204 (1998).

Zyss, J., Ledoux, I., Volkov, S., Chernyak, V., Mukamel, S., Bartholomew, G.P., Bazan, G.C., "Through–Space Charge Transfer and Nonlinear Optical Properties of Substituted Paracyclophane", J. Am. Chem. Soc., vol. 122, No. 48, pp. 11956–11962 (2000).

Wang, S., Bazan, G.C., Tretiak, S., Mukamel, S., "Oligophenylenevinylene Phane Dimers: Probing the Effect of Contact Site on the Optical Properties of Bichromophoric Pairs", J. Am. Chem. Soc., vol. 122, No. 7, pp. 1289–1297 (2000).

Oldham, W.J., Jr., Miao, Y.–J., Lachicotte, R.J., Bazan, G.C., "Stilbenoid Dimers: Effect of Conjugation Length and Relative Chromophore Orientation", J. Am. Chem. Soc., vol. 120, No. 2, pp. 419–420 (1998).

Konig, B., Knieriem, B., de Meijere, A., "Double–Layered 1,4–Distryrylbenzene Chromophores—Synthesis, UV and Fluorescence Spectra", Chem. Ber., vol. 126, pp. 1643–1650 (1993).

Hart, H., Bashir–Hashemi, A., Lu, J., Meador, M., "Iptycenes: Extended triptycenes", Tetrahedron, vol. 42, No. 6, pp. 1641–1654.

* cited by examiner

ORGANIC LIGHT-EMITTING DEVICE USING PARACYCLOPHANE

BACKGROUND OF THE INVENTION

1. Field of the Invention

The present invention relates to an organic light emitting device (OLED) in which paracyclophane or a paracyclophane derivative is used as the emissive layer and/or one or more of the charge transport layers, or as a host material for one or more of such layers.

2. Description of the Related Art

Significant efforts have been expended in developing suitable materials for use in organic light emitting devices (OLEDs). Such devices are commercially attractive because they offer the promise of low-cost fabrication of high-density pixeled displays exhibiting bright electroluminescence with long life times and wide color range.

A typical OLED is fabricated by sandwiching an emissive layer between an anode and a cathode. When a bias is applied across the electrodes, holes and electrons are respectively injected from the anode and cathode into the emissive layer, typically facilitated by hole transport and electron, transport layers adjacent to the respective electrodes. The holes and electrons radiatively combine in the emissive layer and emit light. Improved performance can be obtained if blocking layers are provided to block against the injection of either holes or electrons from the adjoining layer and their subsequent escape from the device. Some of these layers can be combined. For example, a double-layered structure is fabricated from a combined hole-injecting and transporting layer together with a combined electron-transporting and light-emitting layer. Likewise, a triple-layered structure is composed of a hole-injecting and transporting layer, a light-emitting layer, and an electron-injecting and transporting layer.

In addition, it is possible to form these layers from a host material doped with another material designed to achieve the desired effect of the layer (for example, to achieve a hole transport effect, an electron transport effect, or an emissive effect).

Because of consumer expectations of good efficiency, long lifetime and pure color, a need exists for development of suitable materials for the various layers.

SUMMARY OF THE INVENTION

It is an object of the invention to provide an improved OLED in which paracyclophane or paracyclophane derivatives are used as the emissive layer and/or one or more of the charge transport layers, or as a host material for one or more of such layers.

Thus, in one aspect, the invention is an OLED in which an emissive layer is sandwiched between at least a cathode and an anode, and in which the emissive layer includes a paracyclophane or a paracyclophane derivative expressed according to the following general formula (I):

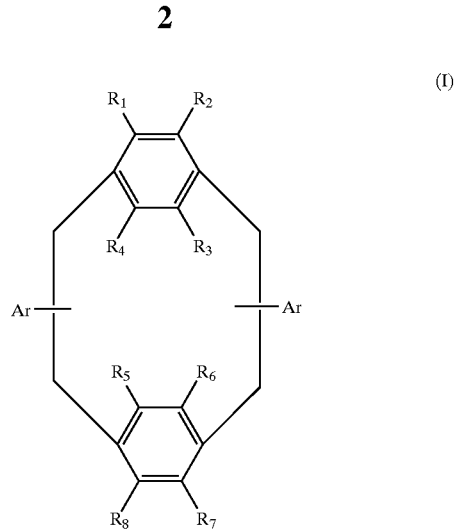

wherein Ar represents aromatics that are present optionally, wherein $R_1$ to $R_8$ are present optionally, and wherein each of $R_1$ to $R_8$ independently represents a hydrogen atom, a halogen atom, a hydroxyl group, a substituted or unsubstituted amino group, nitro group or cyano group, a substituted or unsubstituted alkyl group, a substituted or unsubstituted alkenyl group, a substituted or unsubstituted cycloalkyl group, a substituted or unsubstituted alkoxyl group, a substituted or unsubstituted aromatic hydrocarbon group, a substituted or unsubstituted aromatic heterocyclic group, a substituted or unsubstituted aralkyl group, a substituted or unsubstituted aryloxy group, or a substituted or unsubstituted alkoxycarbonyl group or carboxyl group.

Preferably, the Ar aromatic groups are not present, but if present the groups may be para-bonded or ortho-bonded.

The compound expressed according to formula (I) can be used directly as the emissive layer, or can be used as a host material for an emissive dopant in a case where the emissive layer comprises a paracyclophane host plus an emissive dopant.

In a further aspect, the invention is an OLED having an emissive layer sandwiched between at least one charge transport layer and an anode and a cathode. The charge transport layer can be either an electron transport layer or a hole transport layer, or both. According to this aspect of the invention, the charge transport layer includes a paracyclophane or paracyclophane derivative according to the above general formula (I) wherein Ar and $R_1$ through $R_8$ are specified above.

According to this aspect, the compound expressed according to formula (I) can be used directly as the charge transport layer, or can form a charge transport host material in a case where the charge transport layer comprises a host material plus a charge transport dopant.

This brief summary has been provided so that the nature of the invention may be understood quickly. A more complete understanding of the invention can be obtained by reference to the following detailed description of the preferred embodiment thereof in connection with the attached drawings.

DETAILED DESCRIPTION OF INVENTION

Figure 1:
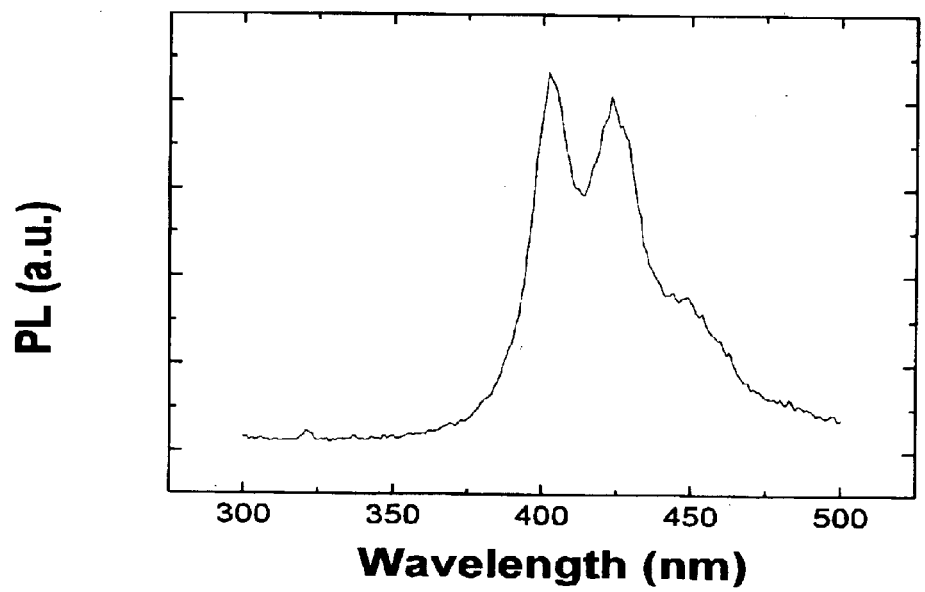
FIG. 1 illustrates the photo luminescence spectrum of an OLED with Compound (IV) in the thin film state.

Paracyclophane and paracyclophane derivatives have the following general structure:

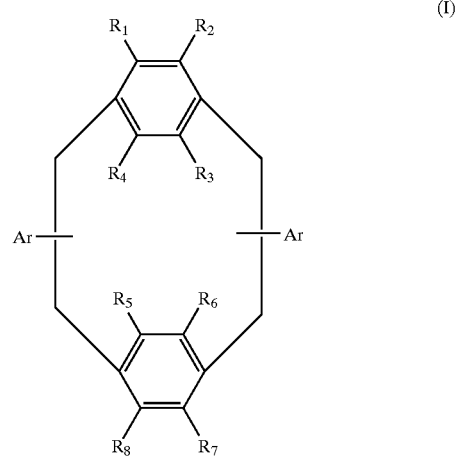

(I)

In the above formula (I), $R_1$, $R_2$, $R_3$, $R_4$, $R_5$, $R_6$, $R_7$, and $R_8$ can be substituted or unsubstituted, depending upon the starting materials used in their synthesis, or to achieve desired properties in the finished material. Substituents may include, without limitation, a hydrogen atom, a halogen atom, a hydroxyl group, a substituted or unsubstituted amino group, nitro group or cyano group, a substituted or unsubstituted alkyl group, a substituted or unsubstituted alkenyl group, a substituted or unsubstituted cycloalkyl group, a substituted or unsubstituted alkoxyl group, a substituted or unsubstituted aromatic hydrocarbon group, a substituted or unsubstituted aromatic heterocyclic group, a substituted or unsubstituted aralkyl group, a substituted or unsubstituted aryloxy group, or a substituted or unsubstituted alkoxycarbonyl group or carboxyl group.

Additionally, in the above formula (I), Ar represents aromatic groups that may be present as an option.

Paracyclophane materials suitable for use with the invention or as starting materials for preparing derivatives according to the invention, can be made using methods known in the art. These methods include, without limitation, Suzuki coupling reactions as disclosed in *Chemical Reviews*, Vol. 95, No. 7, pp. 2457–2483 (1995), incorporated herein by reference, procedures disclosed in *Journal of the American Chemical Society*, Vol. 91, No. 13, pp. 3527–3533 (1969), incorporated herein by reference, and reference procedures disclosed in *Journal of the American Chemical Society*, Vol. 109, No. 9, pp. 2631–39 (1987), also incorporated herein by reference.

An advantage of the disclosed paracyclophane materials for use in OLEDs according to the invention is that these compounds exhibit excellent photo luminescent quantum efficiency. In addition, due to their rigid, cyclic structure, paracyclophane materials are expected to be good hosts for small molecules or metals. Accordingly, paracyclophane materials are expected to exhibit excellent emitting, electron-transporting, and hole-transporting abilities. In addition, because of these properties, a paracyclophane material acting as a host for a functional material is expected to lead to increased performance of an OLED.

General procedures for an OLED fabrication are as follows:

1) Obtain clean ITO substrates coated with a patterned layer.
2) Treat the substrates with $O_2$ plasma for 1–5 minutes.
3) Place the substrates in a thermal evaporator and pump down the pressure below $6 \times 10^{-6}$ torr.
4) Evaporate organic and metallic layers onto the substrates.
   a. A hole transport layer is evaporated with a thickness of ~200 Å.
   b. Usually the emissive layer is evaporated with a host and a dopant. With the shutter closed to prevent premature deposition, the evaporation of the dopant is stabilized at a rate around 0.03 Å/s. Then, the evaporation of the host is stabilized at a rate around 1–3 Å/s, giving a doping concentration of about 1–3%. The shutter is then opened, and deposition is monitored by a quartz crystal monitor. Usually 100–400 Å of the emissive layer is deposited.
   c. The electron transporting material is evaporated at a rate of approximately 1–3 Å/s to form a layer that is usually 200–400 Å thick.
   d. A mask is placed next to the substrates to define where metallic electrodes are to be evaporated.
   e. About 120 Å of a Li—Al alloy is evaporated to improve electron injection into the device.
   f. 1500 Å of Al is deposited, and the evaporator is allowed to cool.
5) Test the devices for luminance, color, and current-voltage characteristics.

Some specific examples of paracyclophanes or paracyclophane derivatives represented by formula (I), that may be used as host materials, electron transporters, hole transporters, and emitters in the present invention, include the following compounds. In addition, these compounds are all symmetric, in that if $R_1$ is present, then $R_7$ is also be present and identical; if $R_2$ is present, then $R_8$ is also be present and identical; if $R_1$ and $R_5$ are present, then $R_3$ and $R_7$ is also present and identical; and if $R_2$ and $R_6$ are present, then $R_4$ and $R_8$ is also present and identical.

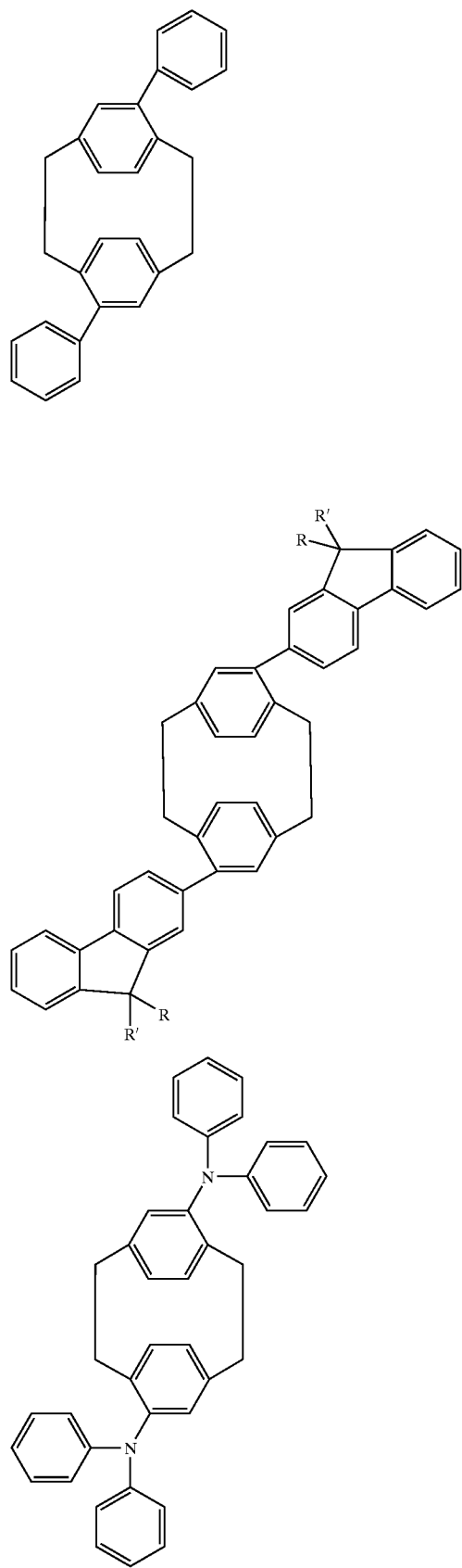
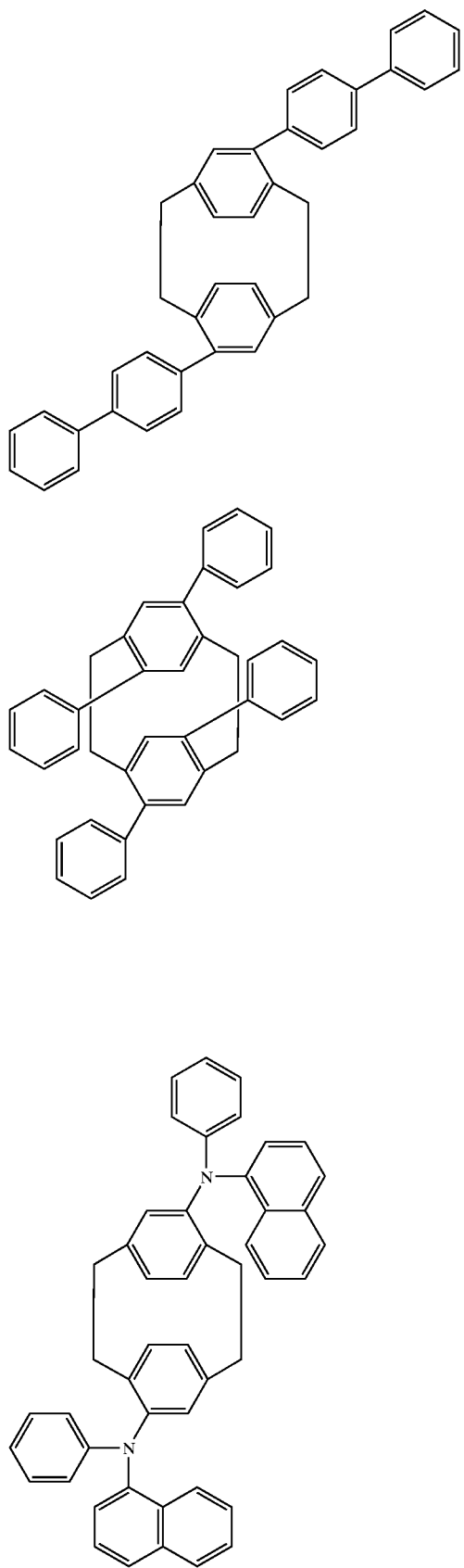

-continued
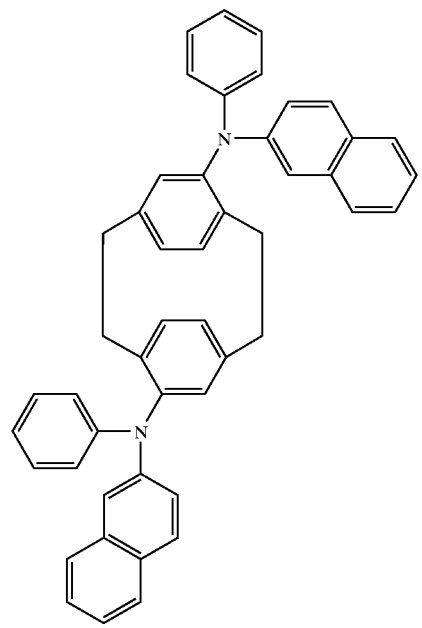
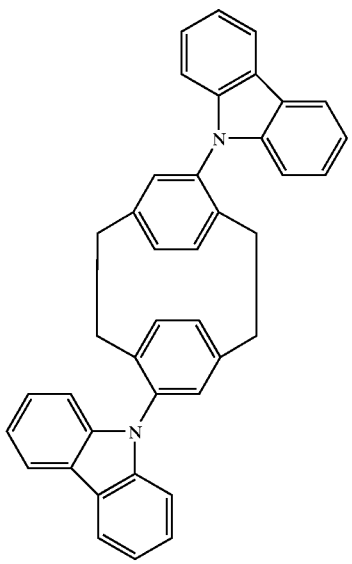
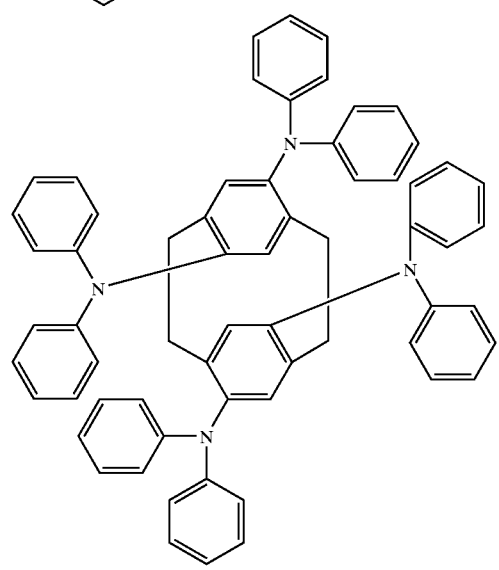
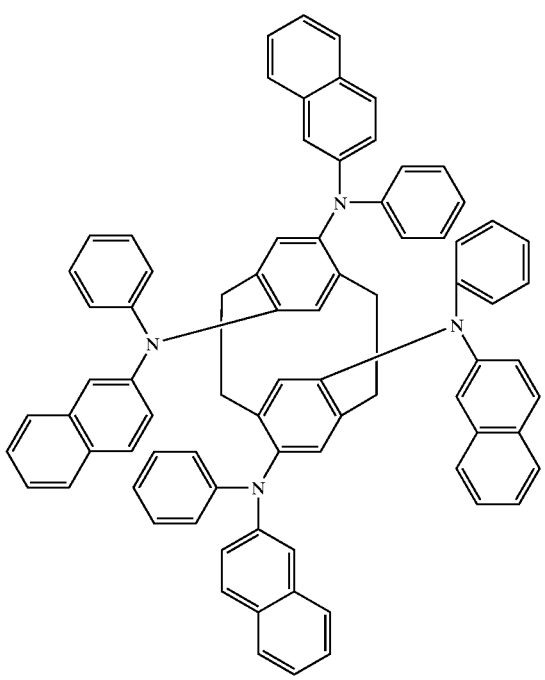
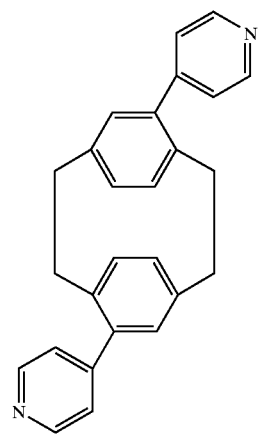
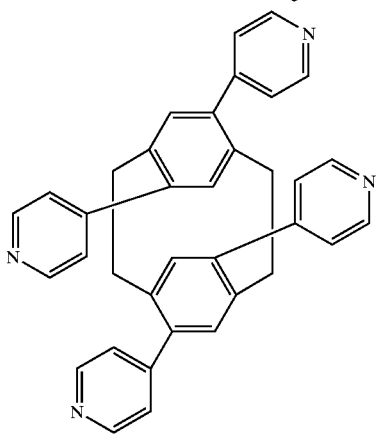

-continued
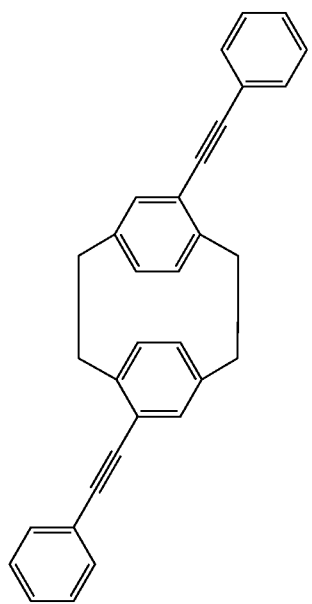
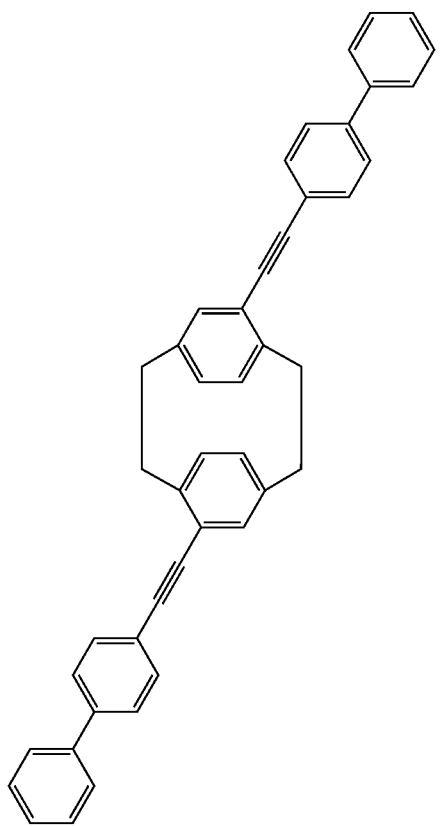
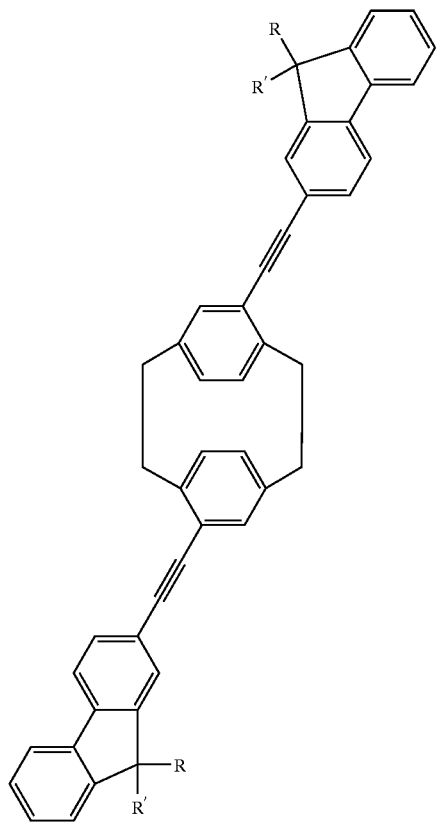
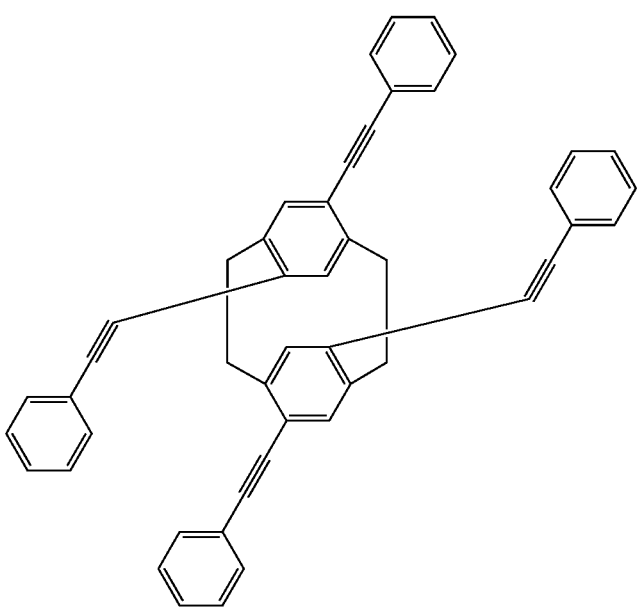

-continued
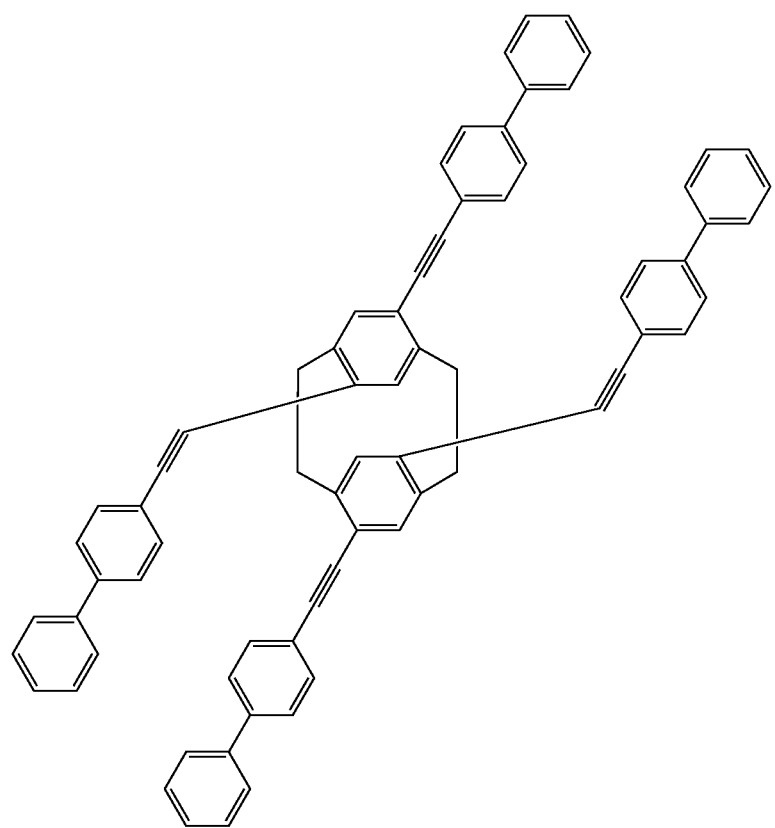
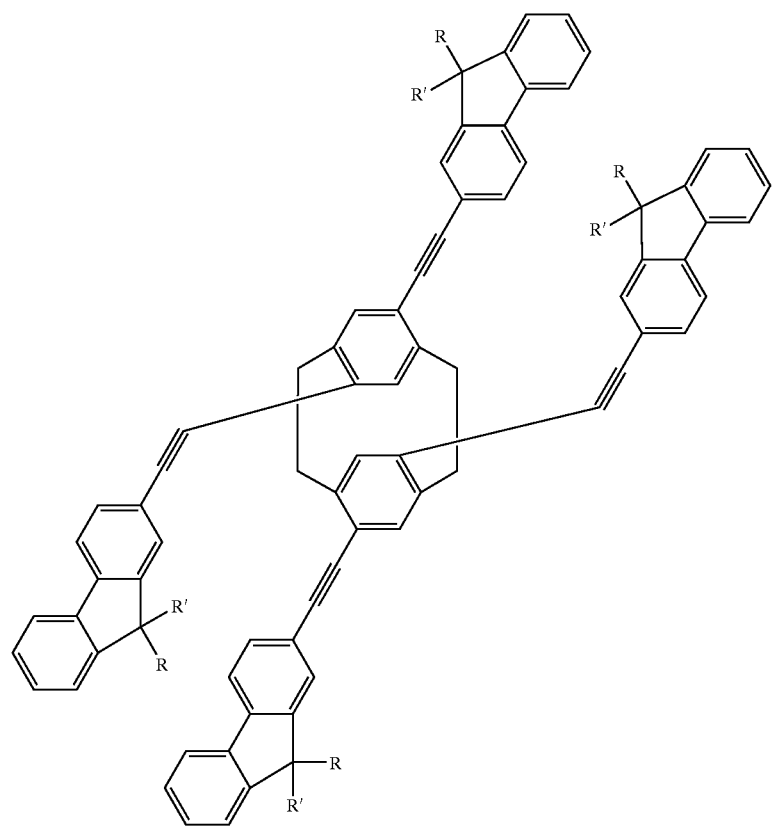

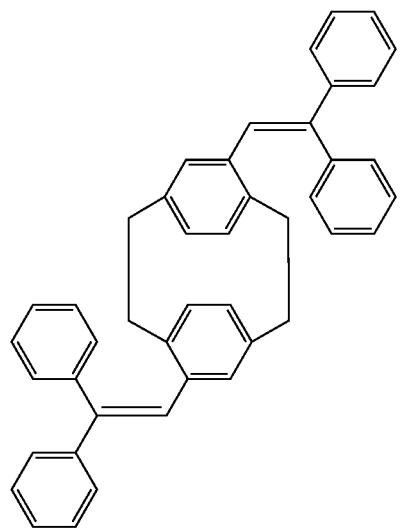
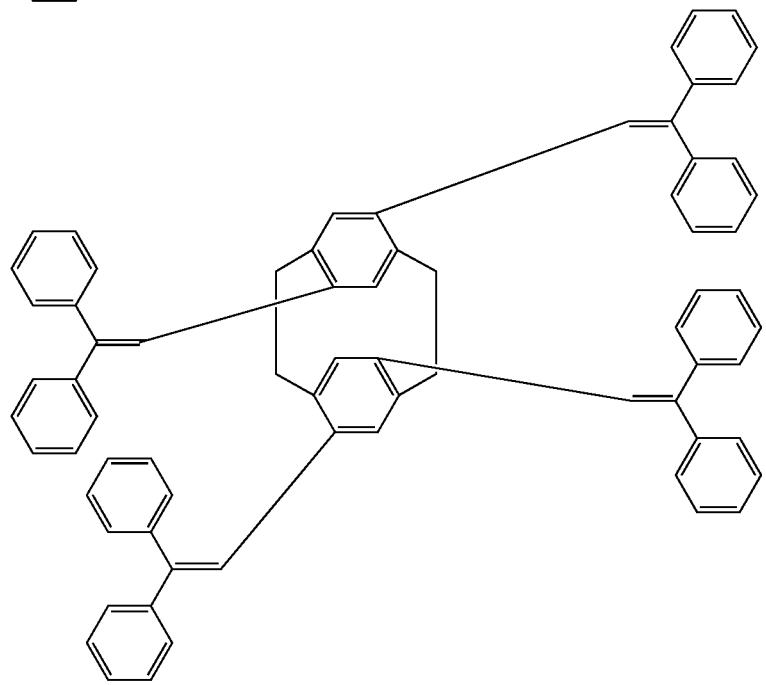
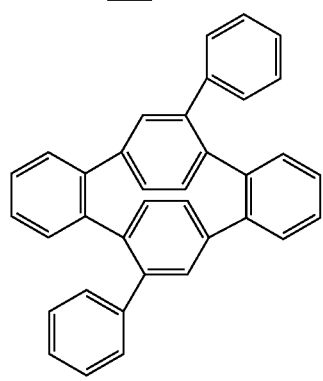
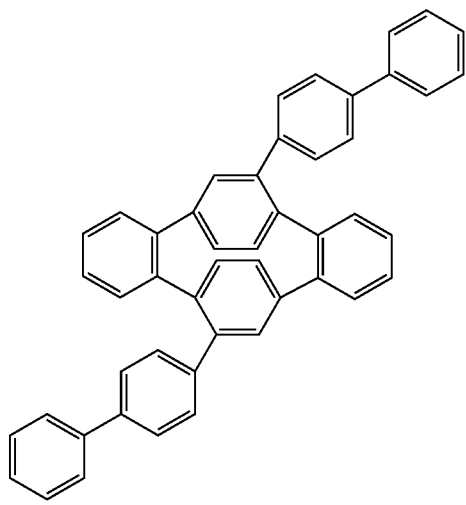

Examples 1–6 show the synthesis of some representative paracyclophanes or paracyclophane derivatives, including non-symmetric structures.

EXAMPLE 1

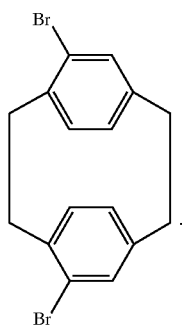
(I)

Compound (I) was synthesized according to the procedures referenced in *Journal of the American Chemical Society*, Vol. 91, No. 13, pp. 3527–3533 (1969) and *Journal of the American Chemical Society*, Vol. 109, No. 9, pp. 2631–39 (1987). Compound (I) is fabricated into an OLED using the above general procedures.

EXAMPLE 2

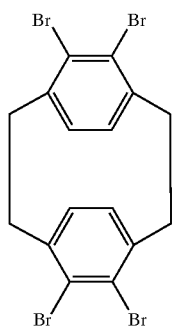
(II)

Compound (II) was synthesized in a similar manner as described in Example 1, with procedures referenced in *Journal of the American Chemical Society*, Vol. 91, No. 13, pp. 3527–3533 (1969) and *Journal of the American Chemical Society*, Vol. 109, No. 9, pp. 2631–39 (1987). Compound (II) was fabricated into an OLED using the above general procedures.

EXAMPLE 3

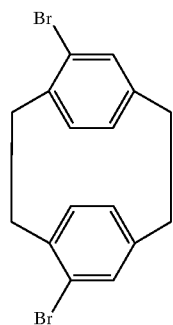
(III)

+

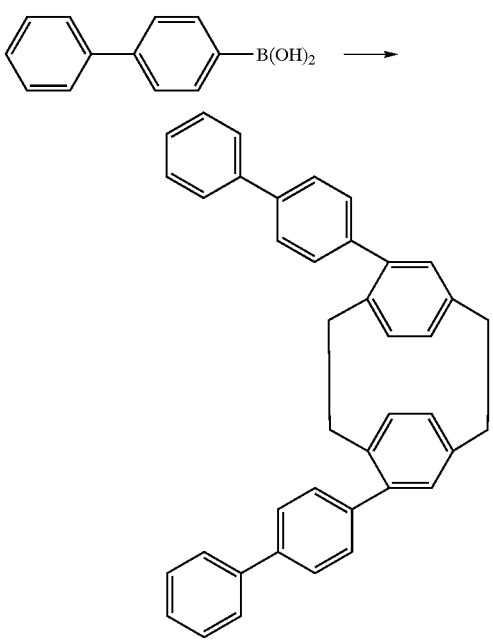

Compound (III) was synthesized using Suzuki coupling reactions. In synthesizing Compound (III), a round flask was charged with pseudo-meta-dibromo-[2,2]paracyclophane (0.26 g, 0.71 mmol), 4-boronic acid biphenyl (0.43 g, 2.2 mmol), Pd(0)(PPh$_3$)$_4$ (100 mg), and a mixture of 20 mL of dry toluene and 10 mL of dry ethanol. After stirring for 10 min at room temperature, a 10 mL solution of the degassed 2M of aqueous Na$_2$CO$_3$ was added to the reaction solution. The reaction mixtures were stirred at 80° C. under N$_2$ for two days. After cooling down, the mixture was poured into water. The product was extracted with toluene, washed with water, and dried over MgSO$_4$. After filtration and concentration, it was purified through column chromatography (Silica gel, mixtures of CH$_2$Cl$_2$/Hexanes). Compound (III) is fabricated into an OLED using the above general procedures.

EXAMPLE 4

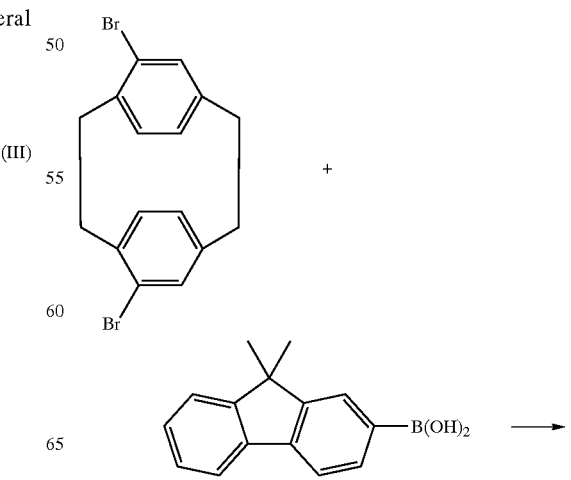
(IV)

+

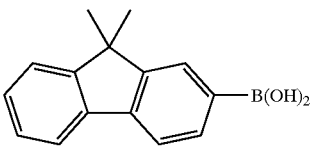

-continued

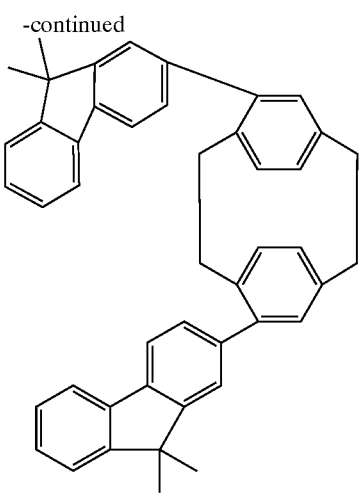

Compound (IV) was synthesized in a similar manner as described in Example 3, using 9,9-dimethyl-2-boronic acid-fluorene instead of 4-boronic acid biphenyl. Compound (IV) was fabricated into an OLED using the above general procedures. The device showed a bright blue emission in its film state. The photo luminescence (PL) spectrum of the device with Compound (IV), in its film state, is shown in FIG. 1.

EXAMPLE 5

Compound (V) was synthesized using Suzuki coupling reactions. In synthesizing Compound (V), n-BuLi (1.6 mL, 2.5 mmol, 1.6 M in hexanes) was added dropwise to a solution of 4,7,12,15-tetrabromo[2,2]paracyclophane (0.4 g, 0.76 mmol) and 11,12-dimethylene-9,10-dihydro-9,10-ethanoanthracene (0.38 g, 1.65 mmol) in 30 mL of dry toluene. The solution was stirred under nitrogen overnight and quenched with a small amount of water. The organic layer was extracted with toluene, washed with water, and dried over $MgSO_4$. After removal of the solvent, the product was recrystallized from $CH_2Cl_2$. Compound (V) is fabricated into an OLED using the above general procedures.

EXAMPLE 6

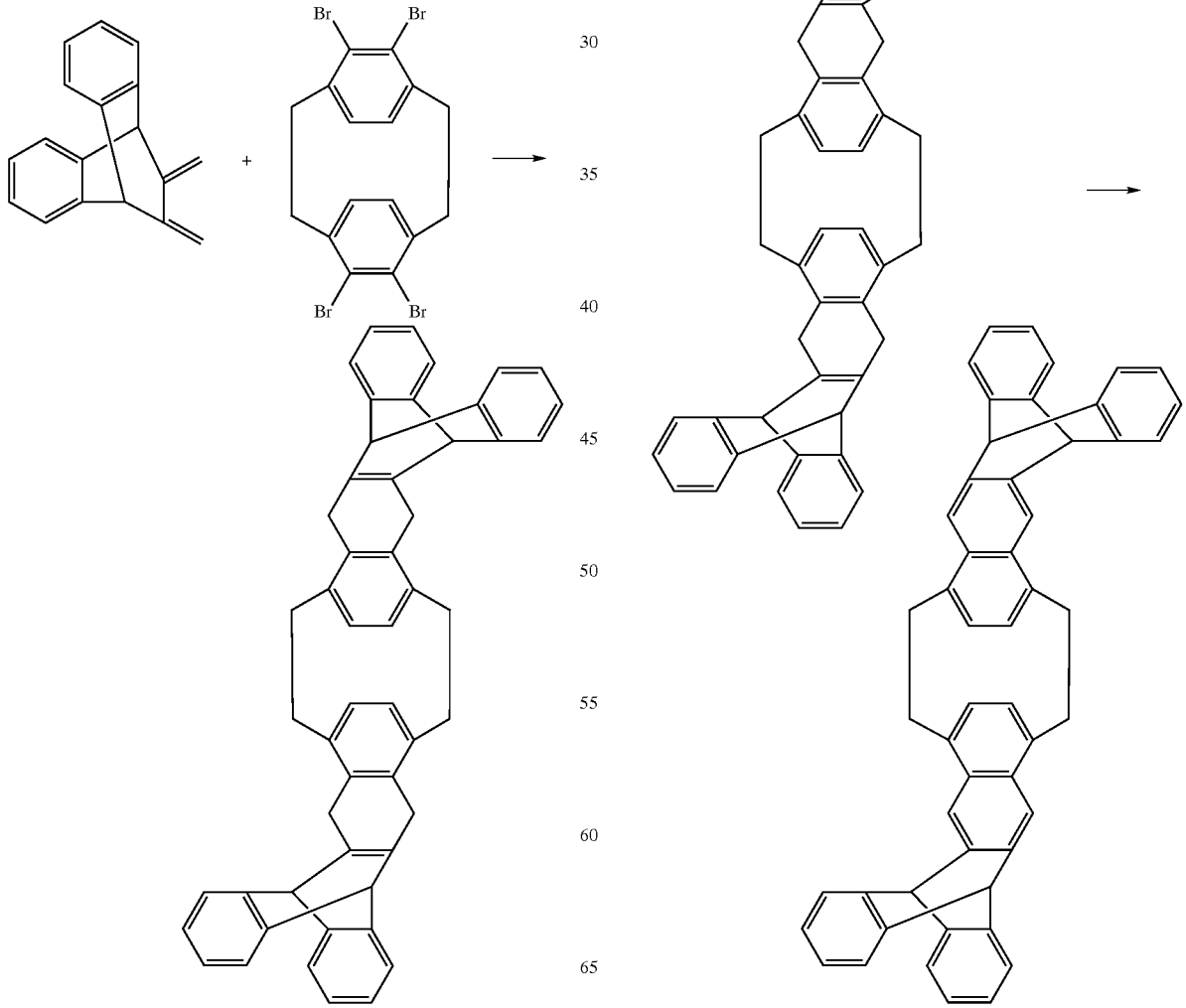

reactions. In synthesizing Compound (VI), Compound (V) (0.2g), 0.1 g of 0.5% Pd/C, and 30 mL of o-xylene were added to a flask. The solution was reflued under nitrogen for two days. The hot solution was filtrated and Compound (VI) was obtained after the solvent is removed by distillation. Compound (VI) is fabricated into an OLED using the above general procedures.

EXAMPLE 7

FIG. 1 schematically depicts an OLED according to the invention, including transparent substrate 1, anode 2 adjacent the substrate, hole transport layer 3 adjacent the anode, emissive layer 4, electron transport layer 5, and cathode 6. Each of these layers may itself comprise multiple layers of material having similar composition or function.

Suitable materials for substrate 1 include glass, quartz and the like, and polymers (including, without limitation, polyesters, polycarbonates, polyacrylates, polymethacrylates, and polysulfones). The thickness of the substrate is not critical and can range, for example, from about 25 to over 1,000 microns, depending on the structural demands of the device.

The anode 2 adjacent the substrate can be comprised of a metal, an alloy, an electroconducting compound, or mixtures thereof, especially with a work function equal to, or greater than about 4 electron volts. Specific examples of anodes include positive charge injecting electrodes such as indium tin oxide (ITO), tin oxide, zinc oxide, gold, platinum, electrically conductive carbon, and conjugated polymers such as polyaniline, polypyrrole, and the like. ITO is preferred. The thickness of the anode can range anywhere from about 10 nanometers to 1 micron.

The hole injecting layer (also referred herein as a hole transport layer) 3 may be comprised of one, two or more hole transport components known in the art. Any conventional known materials which can inject and transport holes into the emissive layer may be employed for forming the hole injecting layer. A preferred hole injecting and hole transporting material is 4,4'-bis [N-(1-naphthyl-1)-N-phenyl-amino]-biphenyl (NPB), having the following structure:

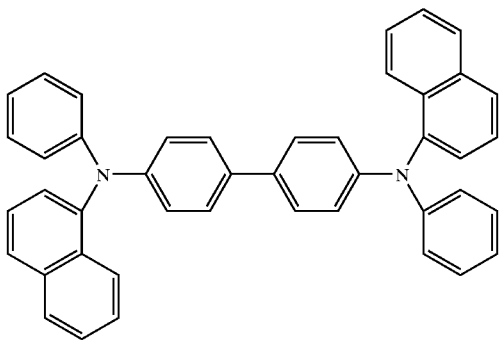

NPB: 4,4'-bis[N-(1-naphthyl-1)-N-phenyl-amino]-biphenyl

The emissive layer 4 may be a deposited neat. One suitable emissive material that may be used in the present invention is a blue emitter. The synthesis of a blue emitter is demonstrated in the following set of reactions:

1)

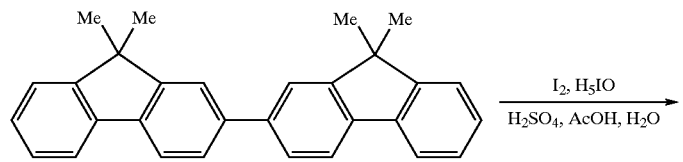

Synthesis of 2, 7-diiododimethylfluorene

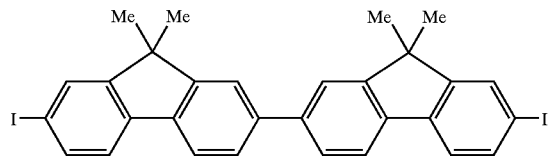

2)

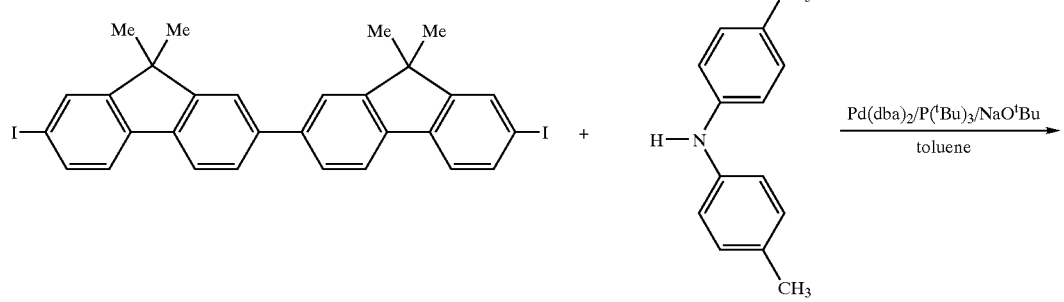

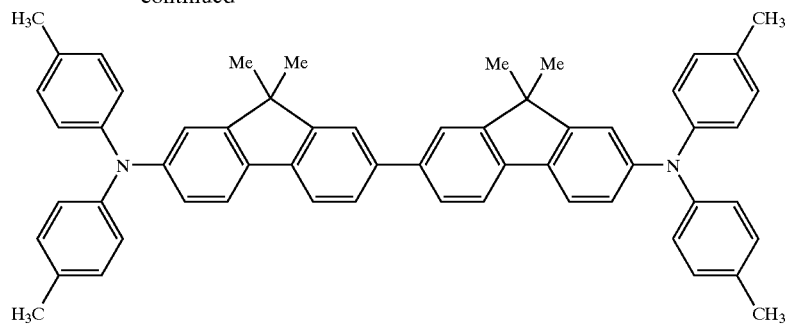

Synthesis of blue emitter

A blue emitter was synthesized using Suzuki coupling reactions. In synthesizing this blue emitter, 76 mg of tris (tert-butyl)phosphine in 3 ml of toluene was added to a solution of Pd(dba)$_2$ (72 mg, 0.125 mmol) in 10 ml of toluene, followed by stirring for 30 min under nitrogen. 2,7-diiododimethylfluorene (360 mg, 0.564 mmol) dissolved in 20 ml of toluene was added to the dark-brown catalyst solution. After stirring the solution for about 20 min, 217 mg (2.26 mmol) of sodium tert-butoxide was added as a solid. The solution was heated on an oil-bath at 80° C. for 5 hours. Next, the reaction mixture was quenched with water. Afterwards, the water phase was extracted with toluene and ethyl acetate. The organic phase was then dried over MgSO$_4$ and then the solvents were evaporated. The product was isolated by silica-gel column chromatography and eluted by a 2:1 (or 3:1) mixture of n-hexane and toluene, yielding a pale yellow solid. If desired, the product may be further purified through repeated silica-gel column chromotography or recrystallization.

In synthesizing the 2,7-diiododimethylflourene used in the synthesis of the blue emitter above, a mixture of H$_2$SO$_4$ (6 ml) and H$_2$O (4 ml) was added to 2FL (350 mg, 0.907 mmol), 164 mg (0.72 mmol) of H$_5$I$_6$O$_6$—H$_2$O, and 366 mg of 12 (2.88 mmol) in 20 ml of acetic acid. The solution was stirred at 80° C. for 3 hours, giving a pale red solution. After cooling the solution to room temperature, water was added. The precipitated solid was filtrated, followed by a washing of the precipitate with water and n-hexane. The product was then dried in a vacuum, yielding a pale red solid. If purified by a silica-gel column, the pale red color is decolorized.

Alternatively, the emissive layer 4 may be a guest-host system. One suitable host material that may be used in the present invention is 9,9-dimethylfluorene-2-boronic acid, which may be synthesized in the following manner:

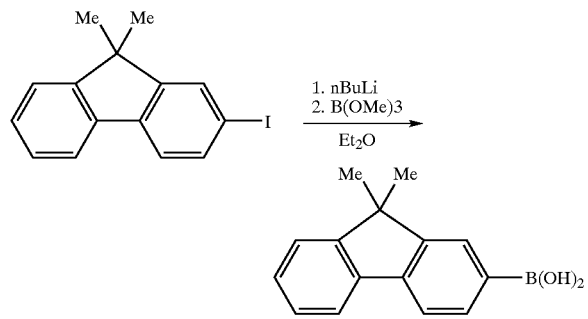

Synthesis of 9,9-dimethylfluorene-2-boronic acid 9,9-dimethyl fluorene-2-boronic acid was synthesized using Suzuki coupling reactions. In synthesizing 9,9-dimethylfluorene-2-boronic acid, 15% n-Butyllithium-hexane solution (35.6 ml, 55 mmol) was added to a solution of 2-iododimethylfluorene (16 g, 50 mmol) dissolved in 170 ml of diethylether on a dry ice-acetone bath at −78° C. under nitrogen. After stirring the slurry solution for 2.5 hours, the reaction mixture was allowed to warm to room temperature, followed by additional stirring for 1 hour. The solution was again cooled on the bath at −78° C. Trimethylborate (27.4 ml, 0.240 mmol) was then added to the solution. The solution was stirred at the low temperature for 1 hour and at room temperature for 1 hour. The resulting reaction mixture was allowed to stand alone at room temperature overnight. Then, a half of the solvent was evaporated, followed by the adding of 50 ml of water. At the same time, 140 ml of 2M HCl aqueous solution was added continuously. The precipitate was filtrated and washed with toluene. The solvent was removed from the organic phase, which gave the additional boronic acid. The solid was also washed with toluene. The product was then dried in a vacuum.

In a guest-host system, it is possible to form the emissive layer 4 from a host material doped with another material designed to achieve the desired effect of the layer (for example, to achieve a hole transport effect, an electron transport effect, or an emissive effect). One suitable dopant that may be used in the present invention is bis (dimethylfluorene), which may be synthesized in the following manner:

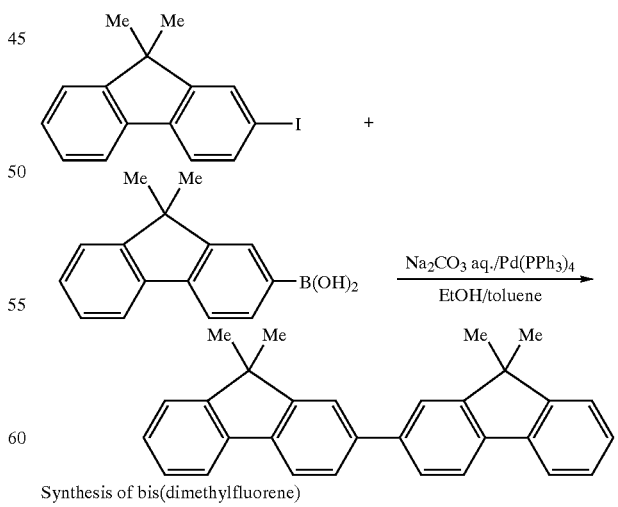

Synthesis of bis(dimethylfluorene)

Bis(dimethylfluorene) was synthesized using Suzuki coupling reactions. In synthesizing bis(dimethylfluorene), 2-Iododimethylfluorene (1.98 g, 6.18 mmol) and 1.5 g (4.73 mmol) of dimethylfluorene-2-boronic acid was dissolved in a mixture of degassed toluene (80 ml) and degassed ethanol (40 ml). Sodium carbonate aqueous solution (41 ml), which was prepared by dissolving 9 g of sodium carbonate in 45 ml of water, was added to the solution, followed by stirring at room temperature for 30 min. To the resulting hazy solution, 238 mg (0.206 mmol) of $Pd(PPh_3)_4$ was added as a solid. The solution was then heated on an oil bath at 80° C. for 5 hours under a nitrogen flow. After cooling to room temperature, ethyl acetate and water were added to the reaction mixture. The organic phase and the water phase were separated. The water phase was extracted with toluene and ethyl acetate. The combined organic phase was dried over $MgSO_4$, and the solvents were evaporated. The desirable product was isolated by a silica-gel column chromatography, and eluted by a 2:1 (or 3:1) mixture of n-hexane and toluene, yielding a white, pale yellow solid. If desired, the product may be further purified through repeated silica-gel column chromatography recrystallization.

Electron transport layer 5 comprises an electron transport material. Given that electron transport capability also can be incorporated into the emissive layer 4 based on paracyclophane materials, the electron transport layer is optional. As an optional electron transport layer, any known electron transport materials can be used. AlQ type materials, such as aluminum tris(8-hydroxyquinoline) and derivatives thereof are particularly preferred. One preferred electron transport material is 4,7-diphenyl-1,10-phenanthroline (Bphen), with the following structure:

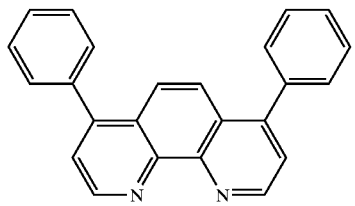

4,7-diphenyl-1,10-phenanthroline (Bphen)

The cathode 6 can be comprised of any metal, including high or low work function metals. Aluminum, lithium, magnesium and calcium are particularly preferred.

Figure 2:
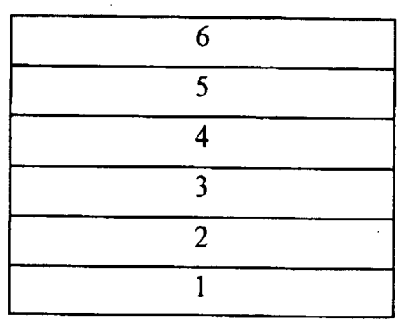
FIG. 2 is a schematic cross-sectional view of an OLED according to the invention.

Referring again to the reference numerals of FIG. 2, an OLED according to the invention was made by first cleaning a glass substrate 1 having an ITO anode 2 patterned thereon in isopropyl alcohol for 5 minutes, followed by rinsing in deionized water for 5 minutes and in isopropyl alcohol again for an additional 5 minutes. The cleaned ITO substrate was treated with $O_2$ plasma and placed in a thermal evaporator, in which the pressure was reduced to $6 \times 10^{-2}$ torr. A layer of NPB was heated and deposited as a hole injection layer 3 by vacuum deposition at a rate of 1–3 nm/sec to a thickness of 20 nm. Next, a layer of Compound (II) and 2% wt. blue emitter was deposited as emissive layer 4 by vacuum deposition at a rate of 3 nm/sec to a thickness of 30 nm, with 9,9-dimethylfluorene-2-boronic acid added as a host and bis(dimethylfluorene) added as a blue dopant. Bphen was deposited as electron transport layer 5 by vacuum deposition to a thickness of 20 nm. Finally, a bilayer cathode 6 was applied comprising a layer of Li—Al (12 nm), to improve electron injection in the OLED, followed by Al (150 nm). A driving voltage was applied and uniform light of blue color was observed. The density of the current produced by the device was 200 $mA/cm^2$ at 7 V. The luminance produced by the device was 1000 cd/m2 at 7 V. The maximum external quantum efficiency was 7%, with the maximum external power efficiency at 0.4 lm/W. The CIE color coordinates were (0.18, 0.11).

The foregoing examples are illustrative only and are not deemed limiting of the invention, which is defined by the claims and is understood to include such obvious variations and modifications as would be obvious to those of ordinary skill in the art.

What is claimed is:

1. An organic light emitting device comprising:

an emissive layer sandwiched between at least a cathode and an anode, wherein the emissive layer includes an organic compound according to the following formula (III):

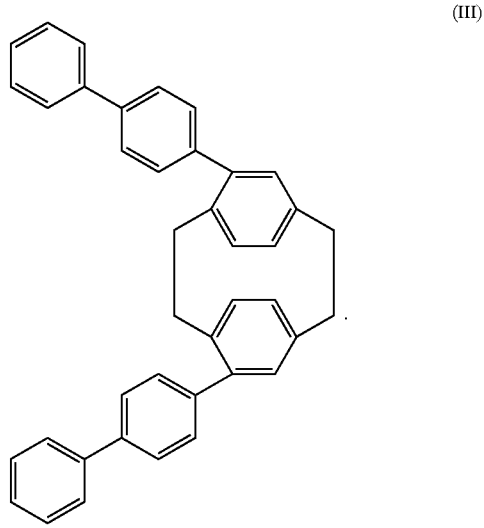

(III)

2. An organic light emitting device comprising:

an emissive layer sandwiched between at least a cathode and an anode, wherein the emissive layer includes an organic compound according to the following formula (IV):

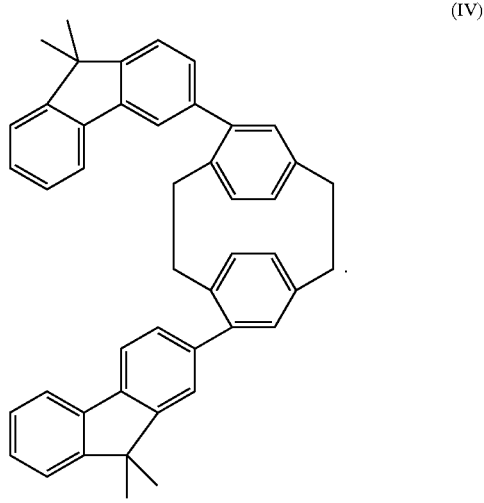

(IV)

3. An organic light emitting device comprising:

an emissive layer sandwiched between at least a cathode and an anode, wherein the emissive layer includes an organic compound according to the following formula (V):

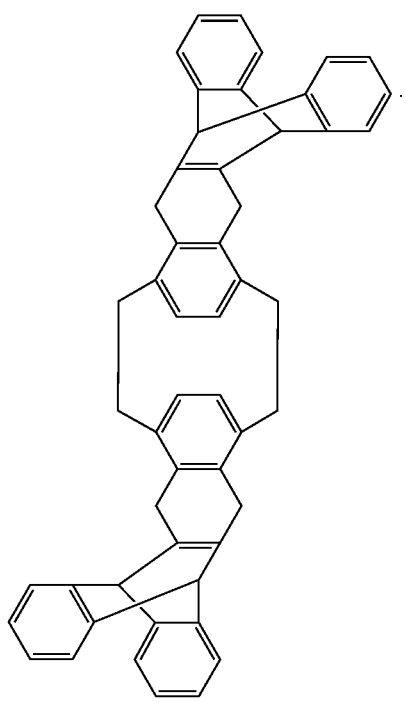

(V)

4. An organic light emitting device comprising:

an emissive layer sandwiched between at least a cathode and an anode, wherein the emissive layer includes an organic compound according to the following formula (VI):

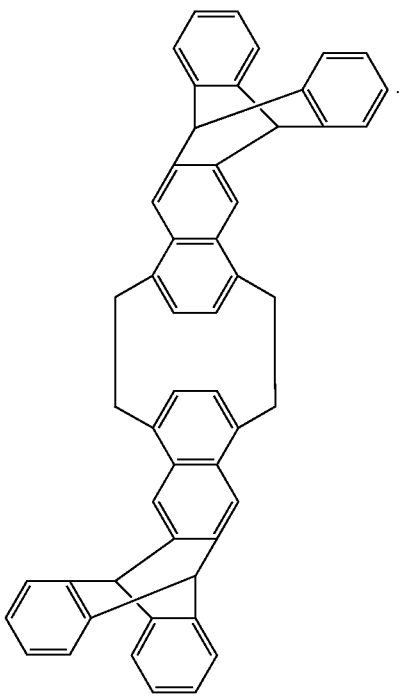

(VI)

5. An organic light emitting device comprising:

an emissive layer sandwiched between at least one charge transport layer and a cathode and an anode, wherein the charge transport layer includes an organic compound according to the following formula (III):

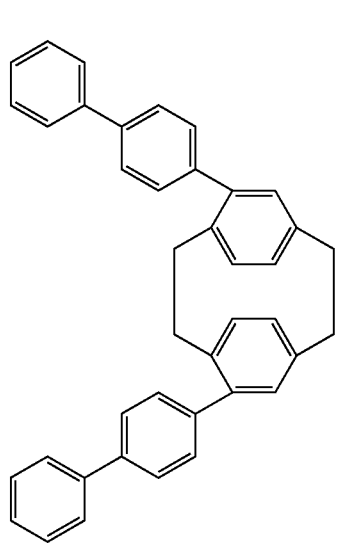

(III)

6. An organic light emitting device comprising:

an emissive layer sandwiched between at least one charge transport layer and a cathode and an anode, wherein the charge transport layer includes an organic compound according to the following formula (IV):

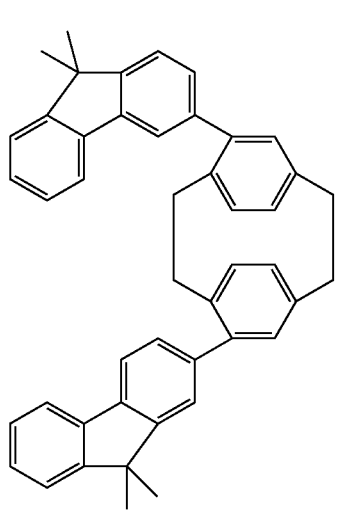

(IV)

7. An organic light emitting device comprising:

an emissive layer sandwiched between at least one charge transport layer and a cathode and an anode, wherein the charge transport layer includes an organic compound according to the following formula (V):

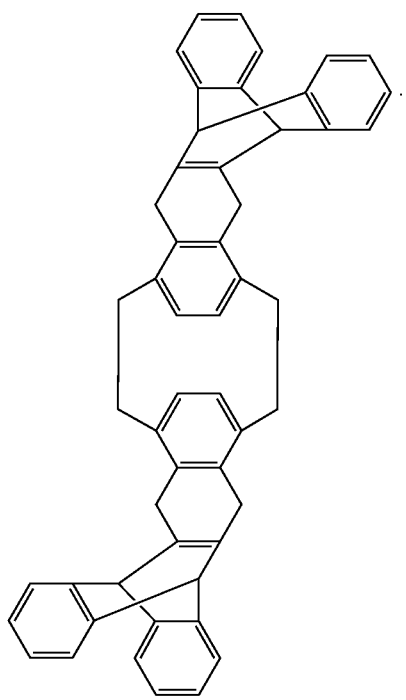
(V)
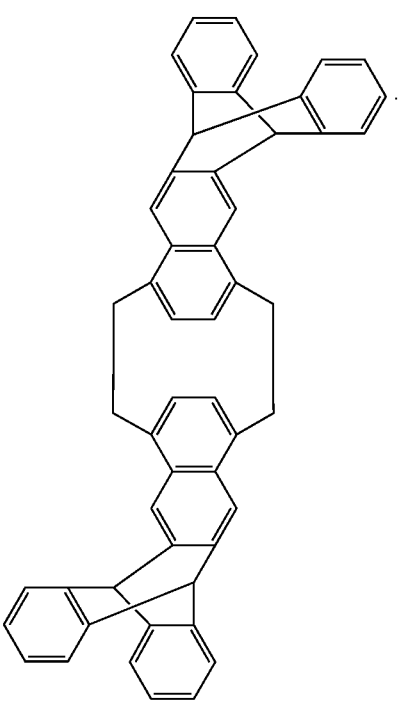
(VI)
8. An organic light emitting device comprising:
an emissive layer sandwiched between at least one charge transport layer and a cathode and an anode, wherein the charge transport layer includes an organic compound according to the following formula (VI):
* * * * *